United States Patent [19]

Cahalan et al.

[11] Patent Number: 5,229,172
[45] Date of Patent: Jul. 20, 1993

[54] MODIFICATION OF POLYMERIC SURFACE BY GRAFT POLYMERIZATION

[75] Inventors: Patrick T. Cahalan, Stein; Michel Verhoeven, Maastricht, both of Netherlands

[73] Assignee: Medtronic, Inc., Minneapolis, Minn.

[21] Appl. No.: 5,698

[22] Filed: Jan. 19, 1993

[51] Int. Cl.$^5$ ............................................. B05D 3/06
[52] U.S. Cl. ................................. 427/536; 427/412.3; 427/412.4; 427/412.5; 427/539; 427/551
[58] Field of Search .................. 427/536, 412.3, 412.4, 427/412.5, 539, 551

[56] References Cited

U.S. PATENT DOCUMENTS

| | | |
|---|---|---|
| 3,826,678 | 7/1974 | Hoffman et al. ............... 117/81 |
| 5,055,316 | 10/1991 | Hoffman et al. ................ 427/2 |
| 5,080,924 | 1/1992 | Kamel et al. ..................... 427/2 |

OTHER PUBLICATIONS

"Surface Modification of Silicone for Tissue Adhesion" by T. Okada et al. in *Biomaterials and Clinical Applications*, Elsevier Science, published in B.V. Amsterda, 1987.

"Graft Copolymerization of Acrylamide onto the UV-Ray Irradiated Film of Polyester-Polyether" by Chen et al., *Journal of Polymer Science*, 6(1):14-190, 1988.

*Primary Examiner*—Bernard Pianalto
*Attorney, Agent, or Firm*—Harold R. Patton; Daniel W. Latham

[57] ABSTRACT

A method for modifying the surface characteristics of a polymeric material by irradiating a surface of the polymeric material in the presence of an oxygen and then grafting acrylamide to the irradiated surface by contacting the irradiated surface with an aqueous solution including acrylamide monomer and ceric ion. Grafted polymer surfaces with dense surface coverage are produced without using a deaerated monomer solution. Biofunctional molecules can be ionically or covalently bonded to the grafted surface.

14 Claims, No Drawings

MODIFICATION OF POLYMERIC SURFACE BY GRAFT POLYMERIZATION

BACKGROUND OF THE INVENTION

The present invention relates to a process for grafting acrylamide onto an polymeric substrate. The invention also relates to a method for improved biocompatibility of polymeric surfaces.

The grafting of a polymer to a polymeric substrate depends on the creation of active sites on the substrate. In general, there are three approaches to creating these active sites so that graft polymerization can occur: chain-transfer activation, radiation or photochemical activation, and chemical activation. Both chain transfer and chemical activation can be applied to either radical or ionic graft polymerization methods.

Activation grafting is the creation of active sites on the substrate by the absorption of radiant energy. Gamma radiation, ultraviolet radiation, corona discharge, radio frequency glow discharge, electron beam radiation or other high energy radiation can be used as the energy source. The activation can be conducted as preirradiation of the polymeric substrate or as mutual irradiation of the polymeric substrate and the monomer to be grafted. By either method, the rate and efficiency of the initiation is dependent upon the type of radiation, the radiation dose (total energy absorbed), the dose rate (rate at which energy is absorbed), and the radiation sensitivity of materials involved. For an example of this method, in U.S. Pat. No. 3,826,678 issued to Hoffman et al., a polymeric substrate is subjected to radiation and thereafter is exposed to a deaerated monomer solution which covalently bonds the monomer to the irradiated surface to produce a surface with improved biocompatibility. Also, for example, Ikada ("Surface Modification of Silicones for Tissue Adhesion" *Biomaterials and Clinical Applications*, Elsevier Science Publishers B.V., Amsterdam, 1987) uses corona discharge to activate surfaces followed by grafting by application of a deaerated aqueous solution of monomers. Also, for example, in U.S. Pat. No. 5,080,924 issued to Kamel et al., radio frequency glow discharge is used to treat a polymeric surface followed by contacting the treated surface with compounds such as acrylic acid in vapor phase to graft pendant carboxyl or amine groups to the polymeric substrate, thereby improving its biocompatibility. However, the effectiveness of radiation grafting to impart improved biocompatibility to some substrates can be quite limited. Silicone-based polymers, polyolefins and fluoropolymers have not proved to be as good substrates for activation grafting with radiant energy as acrylic and styrene-based polymers. Also, the need to eliminate oxygen from any monomer solution used for the grafting process can add greatly to the expense and difficulty of the process.

Chemical grafting is the term applied to grafting reactions involving preformed labile groups either on the backbone or on pendant groups of the substrate, and can be used in the preparation of graft polymers by either free radical or ionic methods. In particular, a free radical reaction mechanism in aqueous solution can be used in which water soluble ethylenically unsaturated monomeric material is grafted onto a substrate, with the free radicals formed on the substrate by an oxidizing metal capable of being reduced by the substrate to a lower valency state (for instance ceric ion). Ceric ion grafting is applicable to a large variety of polymeric backbones, both natural and synthetic. Ceric ion initiated graft polymerization has also been utilized in conjunction with a large number of hydroxyl-, thiol-, and amine- containing polymeric substrates. Ceric ion grafting has been used to improve the biocompatibility of urethane polymers used in blood compatible devices such as artificial hearts, ventricular assist devices and extra-aortic balloons. Again, however, the effectiveness of ceric ion grafting to impart biocompatibility to substrates such as silicone-based polymers, polyolefins and fluoropolymers can be quite limited. And again, the need to eliminate oxygen from any monomer solution used for the grafting process can add greatly to the expense and difficulty of the process.

Ceric ion grafting is known to work best when the monomer does not have a tendency to precipitate with the ceric ion, for instance when used with acrylamide, rather than with monomers which include anionic material since these monomers tend to precipitate in the presence of ceric ion.

Ultraviolet light has also been used with ceric ion grafting of acrylamide to polymeric substrates. In Chen et al, "Graft Copolymerization of Acrylamide onto the UV-Ray Irradiated Film of Polyester-Polyether", Journal of Polymer Science, 6(1):14–19, 1988, both sides of a PBT-PTMG film were exposed to UV light followed by immersion of the film into an aqueous solution of acrylamide and the addition of ceric ammonium nitrate. However, such grafting methods are not surface limited in that the amount of UV light needed to effect the grafting reaction also adversely affects the bulk properties of the substrate material. The grafting technique can also produce an unstable graft with small oligomers that wash off with gentile rubbing. These deficiencies are especially undesirable for grafted materials to be used in implantable medical devices since contact with tissue and body fluids could rapidly remove the grafted material.

In order to provide materials with improved biocompatibility and reduced tendency to cause blood coagulation, it is desirable to prevent the occurrence of physicochemical interactions between polymeric substrates and factors which control processes such as blood and tissue cell reaction, thrombosis, thromboembolization, infection and inflammatory response. Cells in living organisms have chemical constituents on their cell membranes that regulate interactions with blood and other tissues. Highly hydrophilic and/or mobile polymer chains on the surface of a polymeric substrate could provide a surface that limits interactions between living tissues and the substrate. Therefore, graft polymerization utilizing monomers such as 2-hydroxyethyl methacrylate and acrylamide have been proposed. Also of interest for improved biocompatiblity is the adsorption or attachment of proteins or other bioaffecting molecules to the polymeric substrate by which the substrate will either be provided with a passivating layer or with a layer which is physiologically active.

Since the ideal blood-surface interface has long been considered to be the naturally occurring human endothelium, research has also focused on endothelialization procedures. For example, pretreatment of prosthetic vascular graft material with fibronectin, collagen or blood plasma has been found to produce substantial increases in adherence of endothelial cells to the graft. However, substrates such as silicones and fluoropolymers do not allow protein coatings to tightly adhere to their surfaces. One proposed solution to this problem is set forth in U.S. Pat. No. 5,055,316 issued to Hoffman et al. in which the substrate is exposed to a polymerizable gas in the presence of a plasma gas discharge and is subsequently exposed to a protein solution to cause the protein to bind tightly to the substrate.

It is therefore an object of the present invention to provide a method for grafting acrylamide onto a polymeric substrate without the need for a deaerated monomer solution.

It is also an object of the present invention to provide a method for grafting acrylamide onto difficult to graft substrates such as silicones or fluoropolymers.

It is also an object of the present invention to provide a method for grafting acrylamide which preserves the bulk properties of the substrate polymer.

It is also an object of the present invention to provide an acrylamide grafted surface with improved stability and resistance to mechanical wear.

It is also an object of the present invention to provide a grafted surface with improved biocompatibility that may be used for materials to be implanted in humans and animals.

It is also an object of the present invention to provide a grafted surface suitable for attachment of biomolecules and endothelial cells.

BRIEF DESCRIPTION OF THE INVENTION

These and other objects are accomplished by the present invention. We have discovered a method for modifying the surface characteristics of a polymeric material comprising the steps of irradiating a surface of the polymeric material in the presence of an oxygen source by an irradiation method which leaves the bulk properties of the material unchanged and then grafting acrylamide to the irradiated surface by contacting the irradiated surface with an aqueous solution including acrylamide monomer and ceric ion. The acrylamide is grafted by free radical grafting to the irradiated surface. Irradiation methods such as radio frequency plasma, corona discharge and electron beam can be used. Ceric ion can be supplied to the monomer solution by ceric ammonium nitrate.

It has heretofore been accepted that ceric ion-mediated grafting on polymeric substrates takes place primarily via the hydroxyl functionality of the substrate polymer. Therefore, if one wished to provide a dense and strongly attached grafted surface on a polymeric substrate, the substrate would first be oxidized and then reduced to provide a hydroxyl-rich surface. While not wishing to be bound by theory, it is believed that the ceric ion grafting is not essentially accomplished via the hydroxyl groups but rather via other oxygen-containing groups such as the carboxyl and hydroperoxide groups that are produced on polymeric surfaces by irradiation in the presence of oxygen or irradiation followed immediately by exposure to oxygen. Accordingly, with the present invention, graft polymerization by applying a solution containing ceric ion and a solution of acrylamide has been found to produce grafted polymer surfaces with dense surface coverage; a much denser surface coverage for some difficult to graft materials than can be achieved by either the prior art ceric ion or radiation grafting techniques when used individually. Also, with the present invention, the functionality of the substrate material is preserved and the graft is more stable than with grafting techniques utilizing UV light.

While a deaerated monomer solution may be used in the grafting method of the present invention to provide a grafted surface of greater density, unlike prior art methods such as radiation activation grafting and chemical grafting, the use of a deaerated monomer solution is not required. Therefore, a monomer solution which has not been depleted of oxygen can also be used with good results. Thus, the method of the present invention can be used to reduce the cost and manufacturing complexity for grafted surface biomedical devices such as catheters, hollow fiber membranes, wound dressing materials, etc. where manufacturing costs may be critical to providing a marketable surface-modified product.

In another aspect of the present invention, biofunctional molecules such as anticoagulants, thrombolytic agents, procoagulant agents, platelet adhesion inhibitors, platelet activity inhibitors, cell attachment proteins, growth factors/cytokines, wound healing agents, antimicrobial agents, and the like can be ionically or covalently bonded to a polymeric substrate by first using the grafting method of the present invention to provide a surface to which the biomolecule can be adhered. Such molecules can be covalently attached to a grafted surface made according to the present invention in which pendant carboxylic acid or amine groups are reacted with similar groups on the biofunctional molecules. Such molecules can also be ionically attached to a grafted surface made according to the present invention in which a charged surface is provided by the grafted polymer. Chemical spacer molecules can also be ionically or covalently attached between the grafted monomer and the biomolecule if additional spacing is desired between the biomolecule and the grafted surface.

DETAILED DESCRIPTION OF THE INVENTION

The polymeric substrates used in the present invention may be virtually any shape or form, such as powders, plates, strips, films, sheets, fibers, fabrics, filaments, tubing, and cast, extruded or compressed articles, and the like.

The substrate used is a solid polymeric material and may include virtually any natural or synthetic polymer. Such polymeric materials include, but are not limited to, polyolefins such as polyethylene and polypropylene, polyisobutylene and ethylene-alphaolefin copolymers, silicone polymers such as polydimethylsiloxane; acrylic polymers and copolymers, such as polyacrylate, polymethylmethacrylate, polyethylacrylate; vinyl halide polymers and copolymers, such as polyvinyl chloride; fluoropolymers such as polytetrafluoroethylene, chlorotrifluoroethylene, and fluorinated ethylene-propylene; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; natural and synthetic rubbers, including butadiene-styrene copolymers, poly-isoprene, synthetic polyisoprene, polybutadiene, butadiene-acrylonitrile copolymers, polychloroprene rubbers, polyisobutylene rubber, ethylene-propylenediene rubbers, isobutylene-isoprene copolymers and polyurethane rubbers; polyamides, such as Nylon 66 and polycaprolactam; polyesters such as polyethylene terephthalate, alkyd resins; phenol-formaldehyde resins; urea-formaldehyde resins, melamine-formaldehyde resins; polycarbonates; polyoxymethylenes; polyimides; polyethers; epoxy resins, polyurethanes; wool; cotton; silk; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose. The present invention is particularly useful for polymeric substrates that are frequently used in medical applications such as silicone rubbers, polyurethanes, natural rubbers, polyesters, polyolefins such as polyethylenes and polypropylenes, polystyrenes, polyamides, and acrylics.

A clean surface of the polymeric substrate is first irradiated in an ionizing radiation. The type of ionizing radiation selected activates the surface of the substrate to the extent required for grafting; preferably without significantly degrading its bulk properties. Gamma radiation, plasma discharge, electron beam, or corona discharge could be used. This irradiation takes place in the presence of oxygen. The source of oxygen can be, for example, atmospheric oxygen, an oxygen-containing material on the substrate surface or, in some cases, oxygen in the substrate material itself. The total radiation dosage desired may be achieved by varying the time of exposure, the intensity of exposure and the number of exposures, subject, of course, to the retention of the properties of the substrate. The preferred dosage will vary from material to material so that the particular dosage will best be determined empirically by grafting several samples which vary as to the radiation dosages which have been applied.

Plasma treatment will now be described in greater detail as one method of irradiation that can be used. For plasma treatments in accordance with the present invention, a conventional plasma generator may be used. Such generators may include thermal, radio frequency, direct current, audio frequency, and microwave plasmas using internal and external capacitive coupling, inductive coupling, resistive coupling, and waveguide techniques. Electrical excitation may be provided by means of a DC or low frequency AC glow discharge produced by internal electrodes or coupling using inductive or capacitive means with higher frequency power sources from audio frequencies up through radio frequency and into microwave frequencies. Microwave waveguide techniques may also be used. Exemplary of suitable plasma generators include plasma reactors made by Plasma Science, Inc.

The plasma may be generated from virtually any gas which is capable of providing the finished substrate with reactive, oxygen-containing functional groups on the surface. Suitable gases can be, for example, mixtures of oxygen with inert gases such as argon or mixtures of oxygen and nitrogen (e.g. air) and low molecular weight organic compounds of oxygen. Other components may be present in the gas mixture such as hydrogen, and other inert gases such as helium, neon, krypton and xenon.

For plasma treatments in accordance with the present invention, sufficient oxygen may remain in the vacuum chamber after pumpdown to achieve the desired oxygen content even if an inert gas is used to generate the plasma or the exposure of the plasma treated substrate to atmospheric oxygen will be sufficient to provide the desired oxygen content.

Plasma generation for surface modification in accordance with the present invention may be carried out with a wide range of power settings, radio frequencies, durations of exposure, temperatures, and gas pressures. Ranges for these parameters can be measured DC or AC power density levels of from 5 to 30 watts (preferably about 15 to 25 watts), oscillation frequencies up to 13.56 megahertz, durations of 5 seconds to 10 minutes, temperatures of 10° to 40° C., and pressures of 0.04 to 0.40 torr. Gas flow rates may vary from stagnant conditions to several volume replacements per second.

The pumpdown pressure which controls the oxygen concentration may be from about 0.01 to 0.001 torr. Depending on the capacity of the pump, these pumpdown pressures may be reached in about 10 to 30 minutes.

Another preferred irradiation method is corona discharge treatment. The term "corona discharge treatment" as described in connection with this invention means the surface treating process wherein the object of the treatment is subjected to treatment in an atmosphere having a faint glow adjacent to the surface of an electrical conductor at high voltage, and is achieved by applying high voltage between a pair of electrodes in the gas atmosphere with a pressure of about 100 mg Hg to about 3 atmospheres.

The selection of electrodes will be determined largely by the size and shape of the material to be treated. In the case of treatment of film or sheet materials, it is desirable that one of a pair of electrodes be a metallic roll and that the film be treated on the roll guiding the film while any shape such as needle, bar, wire or knife is applicable for use as the other electrode of the pair.

For voltage to be applied between a pair of electrodes, a direct current or an alternating current in virtually any wave pattern can be used. Although the intensity of radiation required can vary according to the object to be treated and its properties, an intensity of radiation in the range of about 0.2 to 1.0 kilowatts has been found to be satisfactory.

"Corona discharge treatment" in accordance with this invention is carried out in an oxygen-containing atmosphere. It can also take place in a mixed-gas atmosphere in which oxygen is present. An atmospheric oxygen concentration can be used.

The resulting polymeric surface modified by exposure to the plasma or corona discharge contains oxygen containing groups, such as carbonyl, carboxyl, hydroxyl, ether and hydroperoxide groups as a consequence of the reaction of the surface with reactive oxygen species.

The present grafting process is carried out on the irradiated substrate in an aqueous solution (20 to 40 wt % of acrylamide monomer) as contrasted with other solvent polymerization processes such as organic solvent polymerization or even bulk polymerization. The monomer to be grafted according to the present invention is acrylamide.

The grafting reaction of the present invention may be carried out at temperatures between about 18° C. and 25° C. The present invention may be carried out under pressure or under partial vacuum, but it is preferred to utilize atmospheric pressure inasmuch as the reaction proceeds very favorably at this pressure. The pH of a grafting solution with ceric ammonium nitrate is typically about 1.4.

The amount of ceric ion utilized in the practice of the process of the present invention can be varied over fairly wide limits. For example, one may utilize from about 0.0001 to 0.002 mole of ceric ion per mole of polymerizable monomer. Preferably one would use between 0.0002 to 0.0005 mole of ceric ion per mole of acrylamide. Ceric ion is preferably introduced into the reaction mixture in the form of a ceric salt. Among the ceric salts adapted for use in the present invention are ceric nitrate, ceric sulfate, ceric ammonium nitrate, ceric ammonium sulfate, ceric ammonium pyrophosphate, ceric iodate, ceric salts of organic acids, such as ceric naphthenate and ceric linoleate and the like. These compounds may be employed singly or in combination with one another.

In general, the time required to achieve a desired degree of polymerization may be determined empirically. Thus, for example, acrylamide may be grafted at different time intervals and the extent of grafting determined by staining of functional groups introduced in the graft by chemical modification. The length of the polymeric chain and graft density may be varied by varying the acrylamide concentration, ceric ion concentration, temperature and the density of reactive groups provided by irradiation on the irradiated substrate.

In another aspect of the present invention, biofunctional molecules (biomolecules) such as anticoagulants (e.g. heparin, heparin sulfate, dermatin sulfate, glycosaminoglycan sequences and analogs, hirudin, thrombin inhibitors), thrombolytic agents (e.g. streptokinase, tissue plasmogen activator), procoagulant agents (e.g. Factor VIII, von Willebrand's Factor, protamine sulfate), platelet adhesion inhibitors (e.g. albumin, albumin adsorbing surfaces, 13-hydroxyoctadecanoic acid, hydrophilic hydrogels, phospholipids), platelet activity inhibitors (e.g. aspirin, dipyrimadole, forskolin), cell attachment proteins (fibronectin, vitronectin, collagen types I-IV, laminin, elastin, basement membrane proteins, fibrin, peptide sequences), growth factors/cytokines (e.g. transforming growth factor beta, basic fibroblast growth factor, platelet derived growth factor, endothelial cell growth factor, gamma interferon), wound healing agents (e.g. hydrogels, collagens, epidermal growth factor), antimicrobial agents (e.g. gentamicin, rifampin, silver salts), anticancer agents (e.g. 5-fluorouracil), hormones (insulin, vasopressin progesterone, human growth hormone), analgesics, detoxification agents (e.g. chelating agents) and the like can be ionically or covalently bonded to a polymeric substrate by first applying the grafting method of the present invention to provide a suitable surface to which to attach the biomolecule. Such molecules can be covalently attached to a grafted surface made according to the present invention in which pendant functional groups such as amine and carboxyl groups introduced in the gel by chemical modification are reacted with corresponding groups on the biofunctional molecules according to methods which are well known by those skilled in the art. Such molecules can also be ionically attached to a grafted surface made according to the present invention in which a charged surface is provided by the grafted polymer. Chemical spacer molecules can also be ionically or covalently attached between the grafted monomer and the biomolecule if additional distance is desired between the biomolecule and the grafted surface. The chemical spacer molecules are therefore at least bifunctional while polyfunctional spacers may be used to provide additional points of attachment.

A preferred way to functionalize the grafted polymer is mild hydrolysis to generate carboxyl groups. To these carboxyl groups biomolecules containing amine functionalities can be coupled using a water soluble carbodiimide. The grafted polymer, previously hydrolyzed, is incubated with the biomolecule and a water soluble carbodiimide in an aqueous solution and allowed to react for several hours during which stable amide bonds are formed. Spacer molecules such as ethylene diamine can also be coupled to the partially hydrolyzed graft using carbodiimide. In a second step, a biomolecule continuing a pendant carboxyl group can then be immobilized, again using carbodiimide.

The following examples provide some specific embodiments of the invention and point out differences between the present invention and prior art grafting methods.

EXAMPLE 1

Grafting not according to the present invention was carried out by corona discharge in the absence of a polyvalent metal ion. Flat sheet samples of silicone, polyurethane and polyethylene were treated by corona discharge. The treated samples were then immersed in deaerated solutions of acrylamide monomer to effect grafting. The grafted samples were then tested to determine whether the monomer had grafted to the surface and whether the surface was stable. Contact angle measurements of the treated materials showed no more than a 10 degree decrease in contact angle from control samples, thereby indicating that very few hydrophilic groups had been formed on the substrate materials. Treated materials were hydrolysis treated by immersion in a bath at a pH of 10.5 and a temperature of 60 degrees C. for 3 hours. Subsequent staining with toluidine blue showed no visible stain, thereby indicating the lack of stainable carboxyl groups on the substrate. FTIR surface analysis of treated samples using a KS-5 crystal with a grazing angle of 70 degrees revealed no amide peaks on prehydrolyzed substrates. Qualitative evaluation of the slippery feel of the materials demonstrated very little effect when compared with control materials.

EXAMPLE 2

Grafting according to the present invention was carried out using corona discharge. Polyurethane, silicone and polyethylene flat sheet samples were corona treated using a Sherman Treaters corona machine type HT3 with an input voltage of 650 volts and an output voltage of 13 KV. Sheet materials were given either 6 passes at 0.25 KW for each side or 12 passes for each side with an electrode distance of 5 mm. The treated sheets were divided into two groups; a first group to be immersed in a deaerated 10 weight % solution of acrylamide monomer and a second group to be placed in a 40 weight % solution of acrylamide (not deaerated) with stirring to which 1.75 ml. of a ceric ion solution (made by mixing 13.7 grams of ceric ammonium nitrate (CAN) and 15.75 grams of fuming nitric acid with water to an aqueous solution volume of 250 ml.) was added per 100 grams of acrylamide solution. The first group of test samples were then allowed to react with the monomer solution without ceric ion for one hour at 50 degrees C. while the monomer solution with ceric ion was allowed to react with the test samples for one hour at room temperature. The test samples were then removed from the monomer solutions and thoroughly rinsed with deionized water. Treated materials were then hydrolysis treated by immersion in a bath at a pH of 10.5 and a temperature of 60 degrees C. for 3 hours. Subsequent staining with toluidine blue showed no visible stain on the first sample group while all of the ceric ion treated samples stained, thereby indicating the lack of stainable carboxyl groups on the substrate in the first group (not using ceric ion) and the presence of stainable carboxyl groups in the second group (using ceric ion). Qualitative testing of the wetting of the test samples showed no noticeable difference between the first group (not using ceric ion) and control samples while the second group (using ceric ion) demonstrated complete wetting. FTIR analysis of the surface of samples from the second group showed amide peaks at 1655 cm−1.

EXAMPLE 3

A first group of polyurethane test samples were treated with corona discharge and ceric ion grafting according to Example 2 while a second group of polyurethane test samples were treated by ceric ion grafting according to Example 2 except that no corona discharge pretreatment of the samples was used. SEM evaluation of the test samples showed equally dense surface coverage in the two groups but a thinner grafted surface for the samples treated by ceric ion alone.

EXAMPLE 4

Polyethylene discs with a diameter of 14 mm were placed into a plasma reactor comprising a bell jar with two internal capacitive electrodes with an RF power source. The reactor was evacuated to 0.027 mbar and then room air was introduced and pressure equilibrated to 0.2 mbar and a plasma was initiated at 30 watts for 10 seconds. A first group of plasma treated discs were placed in a deaerated 10 weight % of acrylamide monomer at 50 degrees C for one hour. A second group of plasma treated discs were placed in a monomer solution with ceric ion as set forth in Example 2. The samples were then removed from the monomer solutions and rinsed thoroughly. Comparative staining tests were conducted as set forth in Example 2 with the result that the first group (grafted without ceric ion) did not stain carboxyl groups while the second group (grafted with ceric ion) did stain carboxyl groups.

EXAMPLE 5

Low density polyethylene sheets were irradiated by electron beam treatment using a 3 MeV accelerator. Sheets were treated with varying dose rates (1 kGray and 3 kGray per pass) and dosages (10 Mrads and 25 Mrads) in air atmosphere, and in N2 blanketed atmosphere. After irradiation, the sheets were grafted in the acrylamide/ceric ion solution of Example 2 except that 6 ml of the CAN solution was added per 100 ml of acrylamide solution. All samples except the highest dose rate and dosage under nitrogen blanket showed grafting by FTIR, contact angle measurement, and staining tests as set forth in Example 2.

EXAMPLE 6

Hytrel polyester sheet material was cleaned with isopropanol and dried. It was then exposed to a corona treatment in a Sherman Treaters HT3 device of 0.4 KW with an electrode distance of 5 mm for 20 passes each side and a table speed of 10 meters per minute. The corona-treated sheet material was immersed in a grafting solution of acrylamide and ceric ion (40 g acrylamide, 60 g deionized water and 6 ml of the CAN solution of Example 2) for 50 minutes. In the resulting grafted sheet, a high density graft was visible and the material was very slippery to the touch. Hydrolysis and staining with toluidine blue also indicated a high density graft.

EXAMPLE 7

Polyethylene and silicone squares about 1 cm by 1 cm were cleaned and dried and exposed to corona treatment on the Sherman Treaters HT3 device at 0.29 KW with 20 passes per side at a table speed of 5 meters per minute and an electrode distance of 5 mm. The samples were immersed in the solution of acrylamide and ceric ion as set forth in Example 6. Contact angle was tested by the sessile drop method on the samples with the results set forth in Table 1.

TABLE 1

| Treatment | Contact Angle Polyethylene | Contact Angle Silicone |
|---|---|---|
| None (control) | 82 | 90 |
| Corona Treated Only | 30 | 55 |
| Corona + Ceric Grafted | 18 | 50 |
| Grafted + Hydrolysis | 19 | 40 |
| Grafted + 14 hours boiling water | * | 25 |

*Complete wetting

EXAMPLE 8

Polyurethane samples made substantially as set forth in Example 2 were provided with covalently attached heparin by carbodiimide attachment. After overnight soaking of the samples in deionized water at 60° C. to remove homopolymer, the grafted polyacrylamide surface was partially hydrolyzed by immersing the test samples in a 0.5M sodium carbonate buffer solution of pH=10.5 at 60° C. for 2 hours. Then ethylene diamine was coupled to the surface by incubating the samples with a mixture of 0.5M ethylene diamine.2HCl and morpholineethanesulfonic acid (MES) with the pH adjusted to 5.0. 1-(3-dimethylaminopropyl)-3-ethylcarbodiimide hydrochloride (EDC) was added to effect coupling of the spacer molecule to the grafted surface. The test samples were immersed in an cold solution (ice bath) of 5 mg heparin (from porcine intestinal mucosa) per ml of buffer solution (0.5M MES; pH=5.0). Water soluble carbodiimide (EDC) was added to a concentration of 0.01M. The test samples were stirred in the solution at 0° C. to 4° C. for 6 hours. The solution was then decanted and the samples were thoroughly rinsed with cold deionized water, 1M NaCl, 1M NaHCO$_3$, and deionized water. The test samples were then immersed in 1M NaHCO$_3$ for 3 hours at 60° C. followed by extensive rinsing with deionized water. The samples were then stored in 0.2M phosphate (pH=6.8) until bioactivity testing. Bioactivity testing was then conducted by determining the extent to which thrombin is deactivated by contact with the antithrombin III applied to the surface.

EXAMPLE 9

Fibronectin was attached to a film grafted according to the present invention. A film was grafted with acrylamide substantially as described in Example 2. The film was placed in a 0.5M MES buffered aqueous solution of 0.5M ethylenediamine.2HCl (pH=5.0). The carbodiimide was added until a final concentration of 0.1M was reached. The film was then shaken in the solution for ½ hour at room temperature. The film was removed and rinsed with deionized water and placed into a borate buffered solution (0.1M) of 0.5 wt % glutaraldehyde (pH=9.0) for one hour at room temperature while being shaken. The film was then removed, rinsed, and placed in a borate buffered solution of 1 wt % polyethyleneimine (pH=9.0) for ¼ hour at room temperature while being shaken. The film was then removed, rinsed, and placed in a borate buffered solution (0.1M) of 0.05 wt % glutaraldehyde (pH=9.0) for ¼ hour at room temperature while being shaken. The film was then rinsed in deionized water. 0.01 g. of lyophilized fibronectin (4.556 wt % fibronectin from human plasma in sodium chloride and HEPES) was dissolved in 1 ml deionized water. 7 ml of phosphate buffered saline (9.0019 g. NaCl, 1.1833 g. KH2PO4, 4.3195 g. NaH2PO4 in 1000 ml of deionized water; pH=7.27) was added and mixed. One ml. of this solution was then used to wet the surface of the film and the film was allowed to incubate for 45 minutes at room temperature. The film was then rinsed and placed in a 0.2M acetate buffered solution of 0.1M sodium cyanoborohydride (pH=4.62) for one hour at room temperature while being shaken. The film was then removed, rinsed with deionized water and stored in a buffered solution of 0.075 wt % NaN3 at room temperature.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. A method for modifying the surface characteristics of a solid polymeric material comprising the steps of;
    (a) irradiating a surface of the polymeric material in the presence of an oxygen source such that the bulk properties of the material are not degraded;
    (b) applying to the irradiated surface an aqueous solution including acrylamide monomer and ceric ion, whereby the monomer is grafted to the irradiated surface.

2. A method according to claim 1 wherein the polymeric material is selected from the group consisting of polyurethanes, silicones, polyolefins, fluoropolymers, polyesters, polyethers, polyamides and blends and co-polymers thereof.

3. A method according to claim 1 wherein the irradiating step is accomplished by an irradiation method selected from the group consisting of plasma discharge, corona discharge, electron beam, and gamma radiation.

4. A method for modifying the surface characteristics of a solid polymeric material comprising the steps of;
    (a) irradiating a surface of the polymeric material in the presence of an oxygen source by an irradiation method selected from the group consisting of plasma discharge, corona discharge, electron beam, and gamma radiation;
    (b) applying to the irradiated surface an aqueous solution including acrylamide monomer and ceric ion, whereby the monomer is grafted to the irradiated surface.

5. A method according to claim 4 wherein the polymeric material is selected from the group consisting of polyurethanes, silicones, polyolefins, fluoropolymers, polyesters, polyethers, and polyamides.

6. A method according to claim 4 wherein the irradiation applied is corona discharge radiation applied to the polymeric material at an intensity in the range of about 0.2 to 1.0 kilowatts.

7. A method according to claim 4 wherein the irradiation applied is a radio frequency plasma applied to the polymeric material at an intensity in the range of about 15 to 25 watts.

8. A method according to claim 4 wherein the irradiation applied is an electron beam applied to the polymeric material at an intensity in the range of about 1 to 3 Kgray.

9. A method according to claim 1 or 4 wherein the acrylamide monomer is at a concentration in the aqueous solution in the range of about 20 to 40 percent by weight.

10. A method according to claim 9 wherein the ceric ion in the solution is at a concentration in the range of about 0.0002 to 0.0005 mole of ceric ion per mole of monomer.

11. A method according to claim 1 or 4 further comprising the step of attaching a biomolecule to the grafted surface.

12. A method according to claim 11 wherein the biomolecule is selected from the group consisting of albumin, fibrinogen fibronectin, heparin, glycoproteins, immunoglobulins, and growth factors.

13. A method according to claim 11 further comprising the step of applying between the grafted surface and biomolecule a coupling agent which is at least bifunctional.

14. A method according to claim 13 wherein the coupling agent is selected from the group consisting of ethylenediamine and polyethyleneimine.

* * * * *